United States Patent
Tennyson et al.

(10) Patent No.: US 12,252,664 B2
(45) Date of Patent: Mar. 18, 2025

(54) FREE FATTY ACID-BASED COMPOSITES

(71) Applicant: Clemson University Research Foundation, Clemson, SC (US)

(72) Inventors: Andrew G. Tennyson, Clemson, SC (US); Rhett C. Smith, Clemson, SC (US)

(73) Assignee: Clemson University Research Foundation, Clemson, SC (US)

( * ) Notice: Subject to any disclaimer, the term of this patent is extended or adjusted under 35 U.S.C. 154(b) by 656 days.

(21) Appl. No.: 16/710,873

(22) Filed: Dec. 11, 2019

(65) Prior Publication Data

US 2020/0190429 A1  Jun. 18, 2020

Related U.S. Application Data

(60) Provisional application No. 62/779,886, filed on Dec. 14, 2018.

(51) Int. Cl.
*C11C 3/00* (2006.01)
*A61L 31/08* (2006.01)

(52) U.S. Cl.
CPC ............. *C11C 3/00* (2013.01); *A61L 31/08* (2013.01)

(58) Field of Classification Search
CPC . C11C 3/00; C23F 11/12; C23F 11/10; C10M 159/00; C10M 141/10; C09F 5/00
See application file for complete search history.

(56) References Cited

U.S. PATENT DOCUMENTS

| | | | | |
|---|---|---|---|---|
| 2,234,545 A | * | 3/1941 | Auer .................. | C09F 5/00 106/249 |
| 2,430,058 A | * | 11/1947 | Klaber .................. | C10M 1/08 252/396 |
| 2,485,341 A | * | 10/1949 | Hand, Jr. ............. | C10M 141/10 508/308 |

(Continued)

FOREIGN PATENT DOCUMENTS

| | | | | |
|---|---|---|---|---|
| WO | WO/2013/070913 | * | 5/2013 | .......... C10M 173/00 |
| WO | WO 2015123552 | | 8/2015 | |

OTHER PUBLICATIONS

R1, Medical device dip molding & molding, Today's Medical Developments, May 2015,. 1-8 (Year: 2015).*

(Continued)

*Primary Examiner* — Dah-Wei D. Yuan
*Assistant Examiner* — Andrew J Bowman
(74) *Attorney, Agent, or Firm* — Joseph T. Guy; Patent Filing Specialist Inc.

(57) ABSTRACT

An improved material, preferably a biomaterial, is provided which is the reaction product of $S_8$ and a free fatty acid or free fatty acid-containing material, preferably in the presence of metal. The improved material can be made by a method comprising reacting $S_8$ with a free fatty acid to obtain a FFA/$S_8$ composite and shaping the FFA/$S_8$ composite into a solid form. The solid form of said FFA/$S_8$ is melted to form melted FFA/$S_8$ and the melted FFA/$S_8$ is optionally applied as a coating on a surface, used as an adjacent material to a surface or the FFA/$S_8$ composite itself is shaped thereby forming a device and preferably a medical device.

4 Claims, 1 Drawing Sheet

Formation of FFA/$S_8$ composite materials

(56) References Cited

U.S. PATENT DOCUMENTS

| | | | | |
|---|---|---|---|---|
| 3,080,330 | A | * | 3/1963 | Rudel ................. C10M 135/14 524/480 |
| 4,481,140 | A | * | 11/1984 | Recchuite .......... C10M 159/123 508/330 |
| 5,880,185 | A | | 3/1999 | Planche et al. |
| 6,524,466 | B1 | * | 2/2003 | Bonaventura ........... A61L 27/50 204/196.12 |
| 2004/0034159 | A1 | | 2/2004 | Brandsch et al. |

OTHER PUBLICATIONS

Wreczycki et al., Sulfur/Organic Copolymers as Curing Agents for Rubber, Polymers, vol. 10, No. 870, Aug. 2018, pp. 1-20 (Year: 2018).*

* cited by examiner

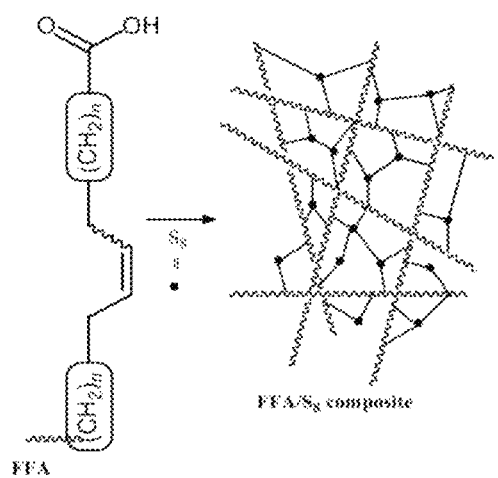
Formation of FFA/S$_8$
composite materials

FREE FATTY ACID-BASED COMPOSITES

CROSS-REFERENCE TO RELATED APPLICATIONS

The present invention claims priority to U.S. Provisional Patent Application No. 62/779,886 filed Dec. 14, 2018 which his incorporated herein by reference in its entirety.

FIELD OF THE INVENTION

The present invention is related to a free fatty acid-based composite which is particularly suitable for biomedical applications and other applications utilizing a coated or adjacent surface. More specifically, the present invention is related to sulfur crosslinked fatty acids, particularly fatty acids obtained as animal rendered materials, which are particularly suitable for many applications including a biomaterial in medical device applications such as for drug delivery, joint lubricants for total joint replacements and other types of medical coatings and adhesives.

BACKGROUND

Medical devices typically utilize stainless steel, titanium, polyethylene, Teflon®, and other artificial materials. Unfortunately, these materials provoke an aggressive immune response in human tissue, referred to in the art as a foreign body reaction (FBR), that causes these materials to degrade and fail over time. There has been an ongoing search for materials which can be used in medical devices which are biocompatible and able to form a barrier, or coating, on medical devices to mitigate or prevent the degradation caused by FBR.

Free fatty acid (FFA)-based biomaterials will not provoke the FBR and thus represent ideal building blocks for use in medical devices such as human medical implant materials. For this reason, FFA-based biomaterials have been developed for applications ranging from drug-delivering stents to artificial joint lubricants, as a barrier, or as coatings, to protect the artificial material. Unfortunately, FFA's by themselves suffer from poor mechanical properties. By themselves, many FFAs are oils or low-melting solids and thus lack the requisite mechanical strength to function independently as biomaterials.

Other applications demand a surface, either as a coating or as an adjacent surface, which has mechanical strength and which his capable of being repaired by thermal processes. Yet another demand is for a material which can function as a portion of a composite, as the major component or minor component, for a variety of applications.

In an effort to strengthen the mechanical properties of FFAs, it is known in the art to crosslink FFAs by oxidative crosslinking technology, wherein new bonds are formed between adjacent molecules. Unfortunately, oxidative crosslinking can produce functional groups that yield radicals in biological tissues and render the oxidatively crosslinked FFA susceptible to digestion. The oxidative crosslinking mechanism shares similarities with the rancidification process. Though somewhat beneficial, oxidative crosslinked FFA is still insufficient due to multiple critical deficiencies. Oxidatively crosslinked FFA crosslinks are mechanically weak and can form radicals which are undesirable in most applications. The oxidative modification of the FFA renders them susceptible to digestion and the oxidized FFAs can cause inflammation that will lead to an aggressive immune response. In non-medical applications the radical may react with other components of the system, or environmental components, which is undesirable. Although existing oxidatively-crosslinked FFA-based biomaterials can be loaded with antibiotics, this strategy is severely limited by the fact that the choice of antibiotic requires foreknowledge of what infection might develop and the antibiotic effect only lasts as long as the drug is present. Once the antibiotic is depleted the antibiotic effect diminishes which allows surviving pathogens or biofilms to reintroduce the infection.

Free fatty acids are typically generated by the hydrolysis of triglycerides. Triglyceride hydrolysis yields a complex mixture of products which is a major cause of quality degradation of animal-derived fats and oils. Because FFAs are more volatile than triglycerides, FFAs give rise to the characteristic unpleasant odors associated with rancidification which provides a rancid free fatty acid. In addition, the hydrolysis of triglycerides is accelerated in the presence of acids so the release of FFAs leads to the faster release of more FFAs. Unsaturated FFAs contain C=C bonds and these groups can react with the $O_2$ in air to release foul-smelling volatile ketones and aldehydes. Both hydrolytic and oxidative pathways contribute to the rancidification of animal-derived fats and oils. Reducing the exposure of fats and oils to moisture and air can decrease the extent of rancidification, but the complete exclusion of water or $O_2$ is impractical on large scales. Therefore, productive uses of FFAs and FFA-containing materials are needed to add value to otherwise undesirable wastes.

There is therefore an urgent need to develop non-oxidative FFA crosslinking strategies to realize the potential of FFA-based products in the biotechnology marketplace and applications such as in a coating or as an adjacent surface. Provided herein is an improved process for the formation of a biomaterial from FFA, particularly FFA obtained by animal rendering, wherein the FFA crosslinking is significantly improved.

SUMMARY OF THE INVENTION

The invention is related to improved materials based on FFA-based composites.

More specifically, the present invention is related to sulfur crosslinked FFA-based composites which are suitable for use in biomedical applications or for use as a coated or adjacent surface.

A particular feature of the invention is the stability of the FFA-based materials.

These and other embodiments, as will be realized, are provided in a material comprising a reaction product of $S_8$ and a free fatty acid.

Yet another embodiment is provided in a medical device comprising a biomaterial comprising a reaction product of $S_8$ and a free fatty acid.

Yet another embodiment is provided in a method for forming a device, particularly a medical device, comprising: reacting $S_8$ with a free fatty acid to obtain a FFA/$S_8$ composite; shaping the FFA/$S_8$ composite into a solid form; preferably melting the solid form of said FFA/$S_8$ to form melted FFA/$S_8$; and applying the melted FFA/$S_8$ to an surface thereby forming a device.

BRIEF DESCRIPTION OF FIGURES

FIG. 1 is a schematic representation of sulfur crosslinking of FFA.

DESCRIPTION

The present invention is related to an improved FFA, particularly an FFA obtained by animal rendering, wherein the FFA is crosslinked with elemental sulfur, Ss.

In the instant invention elemental sulfur, $S_8$, is employed to crosslink unsaturated FFAs, by a mechanism similar to the well-established thiol-ene reaction, referred to herein as thiol-ene-like, thereby generating a crosslinked material referred to herein as an FFA/$S_8$ composite. The FFA/$S_8$ composite is advantageous as it is relatively free from the hazards of degradation and immune response activation. The FFA/$S_8$ composites are expected to be inherently antibacterial and antimicrobial and therefore the FFA/$S_8$ composite are particularly suitable as biomaterials and are likely to provide a transformative advance in human medical device implant technology.

The mechanical stability and thermal recycling properties also allow for improved coatings or for use in adjacent surfaces in many applications.

When compared to the gold standard lubricant, such as for joint replacements, the FFA/$S_8$ composite will likely have lower infection rates due to its innate antimicrobial action and ability to not trigger the FBR. Since fatty acids naturally occur in the body they are far less likely to trigger FBR and therefore the materials are expected to be superior for medical applications.

In the thiol-ene reaction, a thiol ($R^1SH$) reacts with unsaturated, preferably alkene, bonds by the following reaction:

$$R^1SH + HR^2C{=}CR^3H \rightarrow R^1S{-}CR^2H{-}CR^3H_2. \quad \text{Reaction 1}$$

Because the electronegativity of sulfur is nearly identical to that of carbon, the thiol-ene-like reaction represents a non-oxidative crosslinking process. Of particular importance is the fact that $S_8$ is inherently antibacterial and antimicrobial, therefore any $S_8$ crosslinked FFA-based biomaterials will preclude the possibility of patients becoming infected by implanted materials thereby mitigating a leading cause of postoperative infection and implant failure.

By extension of Reaction 1, $S_8$, can react with unsaturated, preferably alkene, bonds by the following reaction:

$$HR^2C{=}CR^3H + S_8 + HR^4C{=}CR^5H \rightarrow H_2CR^2{-}HR^3C{-}S_x{-}CR^4H{-}CR^5H_2 \quad \text{Reaction 2}$$

wherein $S_x$ represents a link comprising x sulfur atoms wherein x is 1-8 and preferable 2-3. $R^2$, $R^3$, $R^4$ and $R^5$ are those groups necessary to form an FFA-based biomaterial of, preferably, different FFA molecules. Groups $R^2$, $R^3$, $R^4$ and $R^5$ may represent those atoms necessary to represent internal disubstituted alkenes, alkenes integral to a substrate with the alkenes external to the substrate, monosubstituted alkenes, disubstituted alkenes, or trisubstituted alkenes. The reaction to form an FFA/$S_8$ composite is illustrated schematically in FIG. 1.

As an alternate to Reaction 2 the sulfur can crosslink two identical alkene molecules or the sulfur can loop back onto the same alkene molecule to make a sulfur ring.

The reaction of sulfur with polyisoprene is illustrated schematically in Reaction 3.

Reaction 3

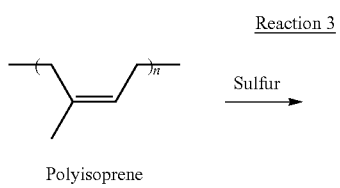

Polyisoprene

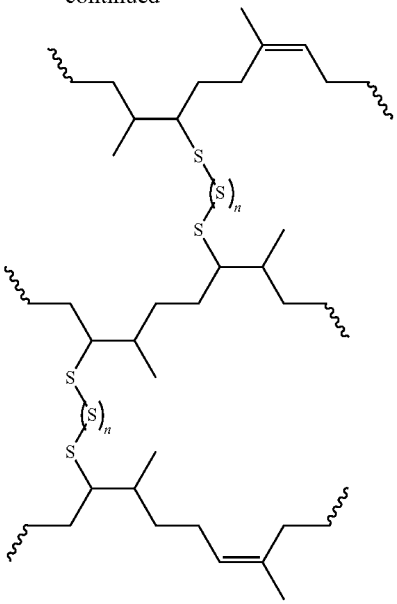

This fatty acid chains crosslinked by elemental sulfur in a thiol-ene-like reaction provides a mechanically robust material. Furthermore, the materials are thermally recyclable without loss of mechanical stability. A particular feature is the ability to self-heal wherein deviations in the material can be removed by thermal treatment. Without limit thereto, the materials can be thermally self-healed at temperatures of 100-120° C. when used as an adjacent material or a coating with the understanding that the temperature will vary based on the presence of additives to the material.

FFA/$S_8$ composites will function as inherently antibacterial/antimicrobial biomaterials thereby enabling their use with implantable human medical devices that are far less likely to lead to infections. The combined biocidel and biocompatible properties of these composites will be entirely unique to the combination of $S_8$ and FFA, given the biocidel activity of the former and the biocompatibility of the latter. Although some existing technologies employ crosslinked FFAs loaded with various drugs, the duration of protection is limited, and the nature of the crosslinks present can cause inflammation, leading to an adverse immune reaction. The synergy between biocompatible FFAs and antimicrobial sulfur afforded by the materials will leapfrog all existing technologies and offer numerous opportunities for biomaterial and human medical device patents.

A feature of the invention is the inclusion of additives which are particularly advantageous when incorporated during the melt-phase to make a composite. Particularly preferred additives are metals, ceramics, cermets, aggregates, lignin-based products, fiberous materials, polymeric based materials, natural or plant-based materials, glasses, inert fillers, antimicrobials, antibiotics and sacrificial materials which can be removed to create porosity. Particularly preferred additives comprise iron, Zn, ZnO, crystalline ceramics, non-crystalline ceramics, gravel, wood, hemp, carbon fibers, fiberglass, and silicon oxide.

Metals are a particularly suitable additive. In the absence of metal salts, the FFA and $S_8$ remain phase-separated and do not mix to a sufficient extent to afford any chemical reactivity. While not limited to theory, it is hypothesized that the COOH group on the FFA is too polar in comparison to the nonpolar nature of $S_8$ thereby inhibiting reaction. When metal salts are added, the COOH groups of the FFAs are hypothesized to bind the metals thereby decreasing the polarity sufficiently to allow them to mix to a sufficient extent to allow reaction with $S_8$. The reaction of oleic acid with sulfur, in the presence of a metal represented as ZnO is illustrated schematically in Reaction 4.

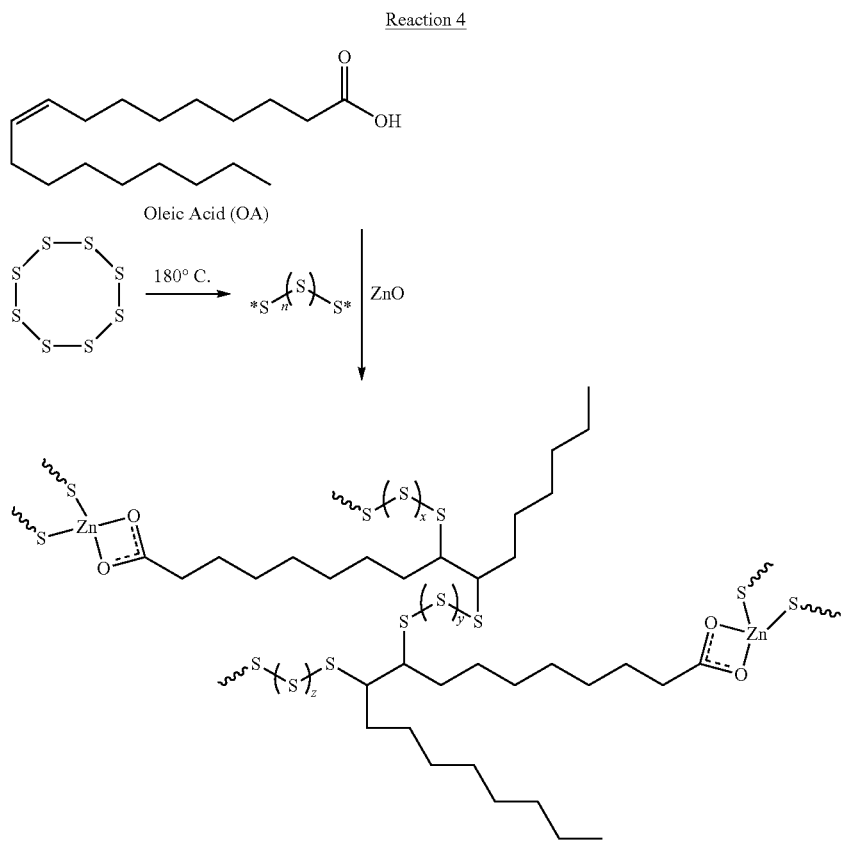

The material can be utilized as a coating wherein the material, with or without additives, is bound to a surface thereby forming a composite. Alternatively, the material can be formed as a distinct formed body wherein the body is used adjacent a surface. An adjacent surface is one wherein the material is in physical contact with the adjacent surface but not bound thereto. A coating is particularly advantageous if the properties imparted by the FFA/$S_8$ are intended to be integral to the coated material. FFA/$S_8$ is particularly advantageous for use with an adjacent surface if the properties of the material are intended to facilitate or alter the movement of the adjacent surface relative to, and independent of, the FFA/$S_8$.

A particular feature of the material is the natural hydrophobicity. A hydrophobic coating, or hydrophobic adjacent surface, can be utilized in many environments. Another particular feature is the ability to alter the hydrophobicity by additives as discussed above.

EXAMPLES

All NMR spectra were recorded on a Bruker Avance spectrometer operating at 300 MHz for protons. Thermogravimetric analysis (TGA) was recorded on a TA SDT Q600 instrument over the range 20 to 800° C., with a heating rate of 5° C. min$^{-1}$ under a flow of $N_2$ (100 mL min$^{-1}$). Differential Scanning calorimetry (DSC) was acquired using a Mettler Toledo DSC 3 STAR$^e$ System over the range of −60 to 130° C., with a heating rate of 10° C. min$^{-1}$ under a flow of $N_2$ (200 mL min$^{-1}$). Each DSC measurement was carried out over three heat-cool cycles to confirm consistent results following the first heat-cool cycle. The data reported were taken from the third cycle of the experiment. Dynamic Mechanical Analysis (DMA) was performed using a Mettler Toledo DMA 1 STAR$^e$ System in dual cantilever mode. DMA samples were cast from silicone resin molds (Smooth-On Oomoo® 30 tin-cure). The sample dimensions were 1.5×8×50 mm. Clamping force was 1 cN·m and the temperature was varied from −60 to 60° C. with a heating rate of 5° C. min$^{-1}$. The measurement mode was set to displacement control with a displacement amplitude of 5 μm and a frequency of 1 Hz. Fourier transform infrared spectra were obtained using a Shimadzu IRAffinity-1S instrument operating over the range of 400-4000 cm$^{-1}$ at ambient temperature using an ATR attachment. Oleic acid (Fisher), zinc oxide (Sigma Aldrich), elemental sulfur (99.5+%, Alfa Aesar) were used without further purification.

Example A—Preparation of Homogenous FFA/$S_8$

A single pure, free fatty acid (FFA) would be obtained in pure form from commercial sources. The FFA would be thoroughly mixed with $S_8$, and the mixture would be heated to higher than 159° C. to open the $S_8$ ring and initiate the thiol-ene-like crosslinking reactions to form the FFA/$S_8$ composites. Because each reaction will use a single FFA in pure form, as opposed to mixtures of multiple FFAs, the composite formed is referred to herein as a homogenous FFA/$S_8$ composite. The molten reaction mixtures would be poured into molds, such as silicon molds, to cast rectangular bars with dimensions appropriate for dynamic mechanical analysis (DMA). Small aliquots of the molten reaction mixtures would be collected and allowed to cool to provide samples suitable for thermogravimetric analysis (TGA) and differential scanning calorimetry (DSC). The TGA experiments would reveal the upper limit of thermal stability for each FFA/$S_8$ composite. The DSC experiments would reveal the temperatures at which glass transitions ($T_g$) and melting ($T_m$) occur. A glass transition occurs when a material changes from crystalline to amorphous. $T_g$ values would be optimized. Optimization insures maximum material flexibility, for use in applications such as membranes or coatings of flexible devices. Alternatively, optimization could be directed to maximum rigidity for applications providing for structural support. Composite $T_m$ values would be optimized to facilitate re-melting and re-molding, while retaining firm structure at target application temperatures. DMA experiments would reveal the mechanical strength of each composite under multiple stress/strain modes under ASTM testing protocols designed to assess long-term durability. Data from TGA, DSC, and DMA experiments would be analyzed as functions of FFA identity and FFA:$S_8$ ratio, to elucidate structure-property relationships. The FFA identity and FFA:$S_8$ ratio would be modulated to achieve optimum thermal stability, $T_g$ and $T_m$ values, and mechanical strength for each composite.

Example B—Testing of Homogenous FFA/$S_8$

Ultimately, the FFA/$S_8$ composite materials would be sold in a solid form preferably selected from pellets, rods, sheets, and blocks, which are typical feedstocks for biomedical device manufacturing and would be particularly well-suited for 3D printing. The homogenous FFA/$S_8$ composites developed under Example A would be designed such that the composite can be re-melted and reshaped to achieve a targeted shape and dimensions. The FFA/$S_8$ composites would be tested to determine the recyclability which is a determination of how closely the properties of the re-melted/re-formed material agree with the properties of the initially-formed material. Consistency (<1% change) in $T_g$, $T_m$, and DMA values across 10 heating/casting cycles would serve as evidence that a given FFA/$S_8$ composite exhibits good recyclability and would allow customers to reshape that product to their design specifications.

Homogenous FFA/$S_8$ composites that exhibit good thermal recyclability would be subjected to a comprehensive battery of ASTM testing methods. Because these composites would be well-suited for a diverse array of applications; such as stents, human implantable medical devices, marine construction, etc.; composites would undergo UV, abrasion, salt spray, scratch resistance, impact, tensile strength, compressive strength, flexural strength, compression, vibration, as well as temperature and humidity cycling preferably using ASTM testing methods.

Example C—Preparation of Heterogenous FFA/$S_8$

Examples A and B involve individual FFAs purchased in pure form, primarily for the purposes of testing and optimization. Commercial rendering processes generate mixtures of multiple FFAs as well as mixtures of FFAs and triglycerides and other biomolecules. Ideally, FFA/$S_8$ composites could be prepared directly from the rendering process from FFA streams without requiring separation and isolation of individual FFA components. The thiol-ene-like reaction will proceed with any alkene present in any unsaturated FFA or triglyceride, so FFA/triglyceride mixtures obtained directly from rendering processes would still afford composite materials upon reaction with Ss. In addition, the thiol-ene reaction and the rancidification process both proceed via radical mechanisms, so even FFA/triglyceride mixtures that have developed unacceptably high levels of rancidity for use in any other application will still react with $S_8$ to afford the same kinds of composite materials suitable for use in biomaterial applications.

Representative samples of FFA, FFA/triglyceride, and rancid FFA/triglyceride mixtures, as generated during a conventional rendering process, would be requested to serve as practical substrates for the $S_8$ crosslinking reactions. Because these reactions would utilize mixtures of FFAs and triglycerides, these products would be referred to herein as heterogenous FFA/$S_8$ composites. Heterogenous FFA/$S_8$ composites would be analyzed by TGA, DSC, and DMA to determine thermal stability, $T_g$ and $T_m$ values, and mechanical strength. Data from these experiments would be analyzed as functions of composition such as; relative amounts of FFA, triglyceride, and rancid material; and FFA:$S_8$ ratio, to elucidate structure-property relationships. Elucidating these relationships would be more complex than in Example A, due to the fact that there are multiple different substrates reacting with $S_8$. It would therefore allow for an understanding of how the individual FFAs affect FFA/$S_8$ composite properties thereby leading to an understanding of how multiple FFA mixtures affect those properties.

Example D—General Synthesis of $ZOS_x$

Elemental sulfur was weighed directly into a reaction vessel equipped with a magnetic stir bar and then appropriate amounts of oleic acid and zinc oxide were added as listed below. The vessel was slowly heated to 180° C. in a silicone oil bath. The reaction mixture was manually stirred for the first 60 min, over which time the sulfur melted and homogenized with the other components. After a period of 24 h, the reaction was removed from the oil bath and allowed to cool to room temperature. Reagent masses and results of elemental combustion microanalysis are provided below. Heating elemental sulfur with organics can result in the formation of $H_2S$ gas. $H_2S$ is toxic, foul-smelling, and corrosive and its generation should be suppressed or it should be trapped as it is formed.

Example E—Synthesis of $ZOS_{99}$

The general synthesis above was used to synthesize $ZOS_{99}$ (99 wt % sulfur) where 36.73 g of elemental sulfur, 0.08 g zinc oxide, and 0.32 mL oleic acid were used in the reaction. Elemental analysis calculated: C: 0.19, H: 0.03, S: 99.69%. Found: C: 0.56, H: 0.0, S: 99.44%.

Example F—Synthesis of $ZOS_{96}$

The general synthesis above was used to synthesize $ZOS_{96}$ (96 wt % sulfur) where 11.74 g of elemental sulfur, 0.14 g zinc oxide, and 0.54 mL oleic acid were used in the reaction. Elemental analysis calculated: C: 2.27, H: 0.36, S: 96.34%. Found: C: 2.69, H: 0.19, S: 96.47%.

Example G—Synthesis of $ZOS_{79}$

The general synthesis above was used to synthesize $ZOS_{79}$ (79 wt % sulfur) where 5.56 g of elemental sulfur, 0.14 g zinc oxide, and 0.54 mL oleic acid were used in the reaction. Elemental analysis calculated: C: 13.17, H: 2.09, S: 78.83%. Found: C: 18.27, H: 2.42, S: 78.83%.

REFERENCES

The following references are incorporated herein by reference.

Reshef, L.; Olswang, Y.; Cassuto, H.; Blum, B.; Croniger, C. M.; Kalhan, S. C.; Tilghman, S. M.; Hanson, R. W., Glyceroneogenesis and the Triglyceride/Fatty Acid Cycle. *J. Biol. Chem.* 2003, 278 (33), 30413-30416.

Anderson, J. M.; Rodriguez, A.; Chang, D. T., Foreign body reaction to biomaterials. *Seminars Immunol.* 2008, 20, 86-100.

Nakagawa, I.; Park, H. S.; Yokoyama, S.; Wada, T.; Yamada, S.; Motoyama, Y.; Kichikawa, K.; Nakase, H., Pretreatment with and ongoing use of omega-3 fatty acid ethyl esters reduce the slow-flow phenomenon and prevent in-stent restenosis in patients undergoing carotid artery stenting. *J. Vasc. Surg.* 2017, 66 (1), 122-129.

Razak, D. M.; Syahrullail, S.; Sapawe, N.; Azli, Y.; Nuraliza, N., A New Approach Using Palm Olein, Palm Kernel Oil, and Palm Fatty Acid Distillate as Alternative Biolubricants: Improving Tribology in Metal-on-Metal Contact. *Tribology Trans.* 2014, 58 (3), 511-517.

Zhang, C.; Madbouly, S. A.; Kessler, M. R., Biobased Polyurethanes Prepared from Different Vegetable Oils. *ACS Appl. Mater. Interfaces* 2015, 7 (2), 1226-1333.

Haman, N.; Romano, A.; Asaduzzaman, M.; Ferrentino, G.; Biasioli, F.; Scampicchio, M., A microcalorimetry study on the oxidation of linoleic acid and the control of rancidity. *Talanta* 2017, 164, 407-412.

Guéraud, F.; Atalay, M.; Bresgen, N.; Cipak, A.; Eckl, P. M.; Huc, L.; Jouanin, I.; Siems, W.; Uchida, K., Chemistry and biochemistry of lipid peroxidation products. *Free Radic. Res.* 2010, 44 (10), 1098-1124.

Lowe, A. B., Thiol—ene "click" reactions and recent applications in polymer and materials synthesis: a first update. *Polym. Chem.* 2014, 5 (17), 4820-4870.

Griebel, J. J.; Li, G.; Glass, R. S.; Char, K.; Pyun, J., Kilogram scale inverse vulcanization of elemental sulfur to prepare high capacity polymer electrodes for Li—S batteries. *J. Polym. Sci. A* 2015, 53 (2), 173-177.

Chung, W. J.; Griebel, J. J.; Kim, E. T.; Yoon, H.; Simmonds, A. G.; Ji, H. J.; Dirlam, P. T.; Glass, R. S.; Wie, J. J.; Nguyen, N. A.; Guralnick, B. W.; Park, J.; Somogyi, A.; Theato, P.; Mackay, M. E.; Sung, Y.-E.; Char, K.; Pyun, J., The use of elemental sulfur as an alternative feedstock for polymeric materials. *Nat. Chem.* 2013, 5, 518-524.

Choudhury, S. R.; Mandel, A.; Ghosh, M.; Basu, S.; Chakravorty, D.; Goswami, A., Investigation of antimicrobial physiology of orthorhombic and monoclinic nanoallotropes of sulfur at the interface of transcriptome and metabolome. *Appl. Microbiol. Biotechnol.* 2013, 97 (13), 5965-5978.

Schneider, T.; Baldauf, A.; Ba, L. A.; Jamier, V.; Khairan, K.; Sarakbi, M.-B.; Reum, N.; Schneider, M.; Roseler, A.; Becker, K.; Burkholz, T.; Winyard, P. G.; Kelkel, M.; Diederich, M.; Jacob, C., Selective Antimicrobial Activity Associated with Sulfur Nanoparticles *J. Biomed. Nanotechnol.* 2011, 7 (3), 395-405.

Faucher, K. M.; Artzi, N.; Beck, M.; Beckerman, R.; Moodie, G.; Albergo, T.; Conroy, S.; Dale, A.; Corbeil, S.; Martakos, P.; Edelman, E. R., Tracking of Drug Release and Material Fate for Naturally Derived Omega-3 Fatty Acid Biomaterials. *Ann. Biomed. Eng.* 2016, 44 (3), 782-792.

The invention has been described with reference to the preferred embodiments without limit thereto. One of skill in the art will realize additional embodiments and improvements which are not specifically stated herein but which are within the scope of the claims as set forth herein.

The invention claimed is:

1. A medical device comprising a reaction product of $S_8$ and a free fatty acid wherein said medical device comprises a surface wherein said free fatty acid is crosslinked by said $S_8$ to form a crosslinked solid coating bound to said surface and wherein said surface comprises a material selected from the group consisting of titanium, polyethylene or polytetrafluoroethylene.

2. A method for forming a material comprising:
    reacting $S_8$ with a free fatty acid to obtain a FFA/$S_8$ composite wherein said free fatty acid is crosslinked by said $S_8$; and
    shaping said FFA/$S_8$ composite into a crosslinked solid form further comprising:
    melting said solid form to form melted FFA/$S_8$; and
    applying said melted FFA/$S_8$ to a surface of a device and cooling thereby forming said material on said device wherein said surface comprises a material selected from the group consisting of titanium, polyethylene or polytetrafluoroethylene.

3. A method for forming a material comprising:
    crosslinking a free fatty acid with $S_8$ to obtain a crosslinked FFA/$S_8$ solid composite; and
    shaping said FFA/$S_8$ composite into a solid form further comprising addition of an additive to said material wherein said additive is selected from the group consisting of metals, ceramics, cermet, aggregates, lignin-based products, fiberous materials, polymeric based materials, glasses, inert fillers, antimicrobials, antibiotics and sacrificial materials.

4. The method for forming a material of claim 3 wherein said additive is selected from the group consisting of iron, Zn, ZnO, crystalline ceramics, non-crystalline ceramics, gravel, wood, hemp, carbon fibers, fiberglass, and silicon oxide.

* * * * *